United States Patent
Busiashvili

(10) Patent No.: US 11,517,704 B1
(45) Date of Patent: Dec. 6, 2022

(54) WRISTBAND CAPSULE CRUSHER

(71) Applicant: Stat Capsule Inc., Glendale, CA (US)

(72) Inventor: Yuri Busiashvili, Pacific Palisades, CA (US)

(73) Assignee: Stat Capsule Inc., Glendale, CA (US)

( * ) Notice: Subject to any disclaimer, the term of this patent is extended or adjusted under 35 U.S.C. 154(b) by 0 days.

(21) Appl. No.: 17/457,692

(22) Filed: Dec. 6, 2021

(51) Int. Cl.
*A61M 21/00* (2006.01)
*A45F 5/00* (2006.01)

(52) U.S. Cl.
CPC ............ *A61M 21/00* (2013.01); *A45F 5/00* (2013.01); *A45F 2005/008* (2013.01); *A61M 2021/0016* (2013.01); *A61M 2021/0083* (2013.01)

(58) Field of Classification Search
CPC .......... A61M 21/00; A61M 2021/0016; A61M 2021/0083; A45F 5/00; A45F 2005/008
USPC .................................................... 128/203.24
See application file for complete search history.

(56) References Cited

U.S. PATENT DOCUMENTS

| | | | | |
|---|---|---|---|---|
| 4,627,432 | A * | 12/1986 | Newell | A61M 15/0003 222/88 |
| 2005/0081856 | A1* | 4/2005 | Cheng | A41D 13/1192 128/205.25 |
| 2006/0157578 | A1* | 7/2006 | Harada | A61L 9/12 239/34 |
| 2010/0323155 | A1* | 12/2010 | Desideria | A61F 13/0283 428/323 |
| 2014/0193764 | A1* | 7/2014 | Pizzini | A61M 15/085 432/247 |
| 2016/0174694 | A1* | 6/2016 | Metzger | A61L 9/12 224/191 |
| 2018/0056013 | A1* | 3/2018 | Knowles | A61M 15/08 |
| 2018/0071466 | A1* | 3/2018 | White | A44C 5/003 |
| 2020/0305559 | A1* | 10/2020 | Eberra | A44C 15/002 |

\* cited by examiner

*Primary Examiner* — Sunita Reddy
(74) *Attorney, Agent, or Firm* — Ralph D Chabot

(57) ABSTRACT

A device comprising a wristband for housing an ammonium inhalant capsule whereby a wearer can self administer an ammonium inhalant to prevent syncope. The wristband comprises a sleeve for receiving an ammonium capsule and a cradle to fracture the capsule for release of the ammonia inhalant.

2 Claims, 3 Drawing Sheets

WRISTBAND CAPSULE CRUSHER

FIELD OF THE INVENTION

The present invention relates to the field of heart condition treatment.

BACKGROUND

In acute cardiovascular crisis, such as cardiac arrest, asystole, brady-tachy-arrhythmia, hypertensive crisis, acute coronary syndrome, or angina, immediate intervention is required to prevent heart attack, cardiovascular collapse, stroke or death. Seconds and minutes may decide between life and death.

When there is no pulse, there is no perfusion of the vital organs, including the brain, the most sensitive end organ. Within seconds of a pulseless condition, a person standing will fall to the ground unconscious. After 10-15 seconds, the condition qualifies as a cardiac arrest.

A substantial, sudden drop of arterial systolic blood pressure (SBP) and heart rate (HR) can result in syncope.

For example, in micturition syncope, arterial blood pressure and heart rate suddenly drop during urination and the person may suddenly lose consciousness, drop to the floor and sustain serious injury, before gaining consciousness.

Another example is nitroglycerin used for chest pain, angina, and acute coronary syndrome and is typically sublingually administered as a bolus. As a result of rapid absorption of the entire bolus dose over very short period of time, and a sudden drop of SBP and HR, syncope is a common result of the nitroglycerin sublingual therapy.

Another common example of loss of consciousness, syncope or cardiac arrest is bradycardia-tachycardia variety of sick sinus syndrome, when rapid atrial arrhythmia, such as rapid fibrillation or flutter, which may suppress sinus node and result in a long asystole at the time of conversion to a normal sinus rhythm. Patients lose consciousness and drop to the floor, sustaining injuries which oftentimes require evaluation and treatment at a hospital.

For prevention and treatment of syncope caused by sudden profound hypotension, bradycardia, or asystole associated with a pulseless condition longer than 3 seconds, ammonia inhalants such as aromatic spirits of ammonia derived from the active compound ammonium carbonate have been used to revive the person from syncope. When the ammonia vapor reaches the nasal cavity, the individual's olfactory reflex activates an adrenaline release intrinsically, within a second or two, via an unconditional reflex on the subcortical level, and prevents prolonged asystolic pause and cardiac arrest.

A need exists for a patient to be able self-administer an ammonia inhalant when sensing a precipitous blood pressure drop and prevent a fainting episode or syncope from occurring.

SUMMARY OF THE INVENTION

Described herein is a wearable device by which a wearer can self-administer an ammonium inhalant to prevent syncope.

The device comprises a wristband having a sleeve for receiving between the sleeve and wristband a cradle and a capsule of an ammonium inhalant; alternatively referred to as smelling salts. The capsule is positioned upon the cradle for subsequent fracture for releasing ammonia vapor. The wristband can be designed to be either single-use or reusable. The sleeve can be made of any material but preferably, it is made from an elastic, breathable material. Elasticity permits the capsule and cradle to be more easily positioned within the sleeve and thereafter snugly secured to the device. Breathable material permits the ammonia vapor escaping from the fractured capsule to more easily vent.

Various means could be utilized to fracture the ammonium capsule including an electrically activated solenoid. Another means is by the wearer mechanically fracturing the capsule.

The wearer, upon sensing the onset of a syncope event, fractures the capsule, releasing the ammonium vapor and brings the wristband closer to the nose for inhalation of the vapor.

One embodiment for the cradle comprises a curved center portion having opposite ends with the inner surface of the curved center portion defining an inner wall and a wing extending from each opposite end. The term wing is also referred herein as a flared end. The cradle is preferably made of a resilient plastic and manufactured from an injection molding process. The cradle is sized to transversely receive a capsule containing an ammonium inhalant. The resilient plastic would be sufficiently rigid so that a force can be applied to the wings by a thumb and index finger, pinching the wings toward one another, which in turn would cause the curved center portion to impart a compressive force upon the capsule for fracture. For this embodiment, the sleeve further comprises a pair of slits so that each wing can be extended through a respective slit when the cradle and capsule are positioned within the sleeve.

More preferably the inner surface of the curved center portion further comprises at least one projection extending from the inner wall a slight distance sufficient to more easily fracture the capsule when a compressive force is applied as the wings are displaced towards each other. Additionally, each wing can incorporate at least one friction rib which allows the wearer to more easily grip each wing with thumb and index finger.

DETAILED DESCRIPTION OF THE PREFERRED EMBODIMENT

The figures presented herein are for illustrative purposes and the illustrated parts are not necessarily shown in correct proportion or scale.

Figure 1:
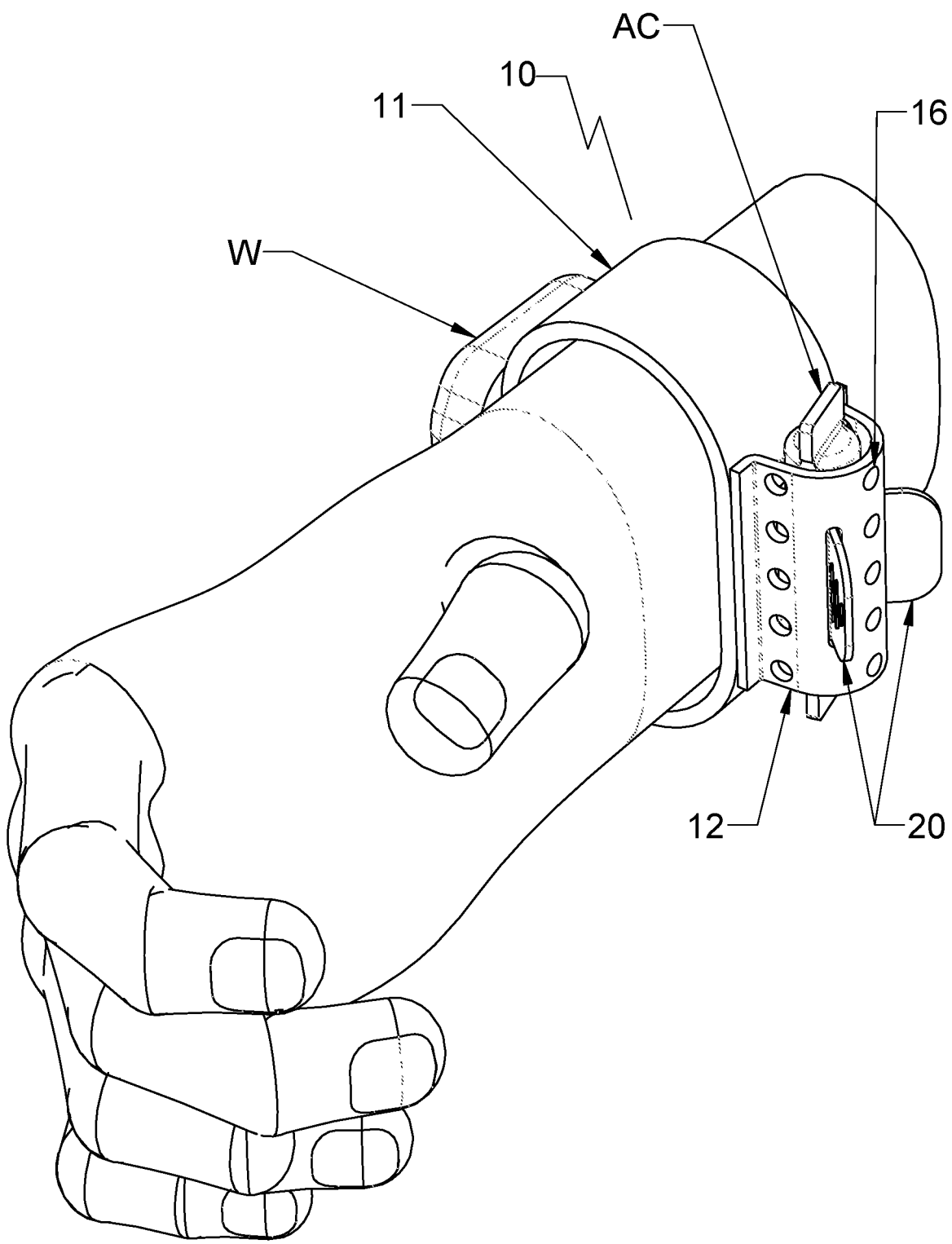
FIG. 1 illustrates the wristband attached about a human wrist.

Device 10 is generally shown in FIG. 1 and is worn about a human wrist and comprises wristband 11 which can be designed for attachment to a timepiece or heart rate monitor W although neither is necessary to practice the invention.

Figure 4:
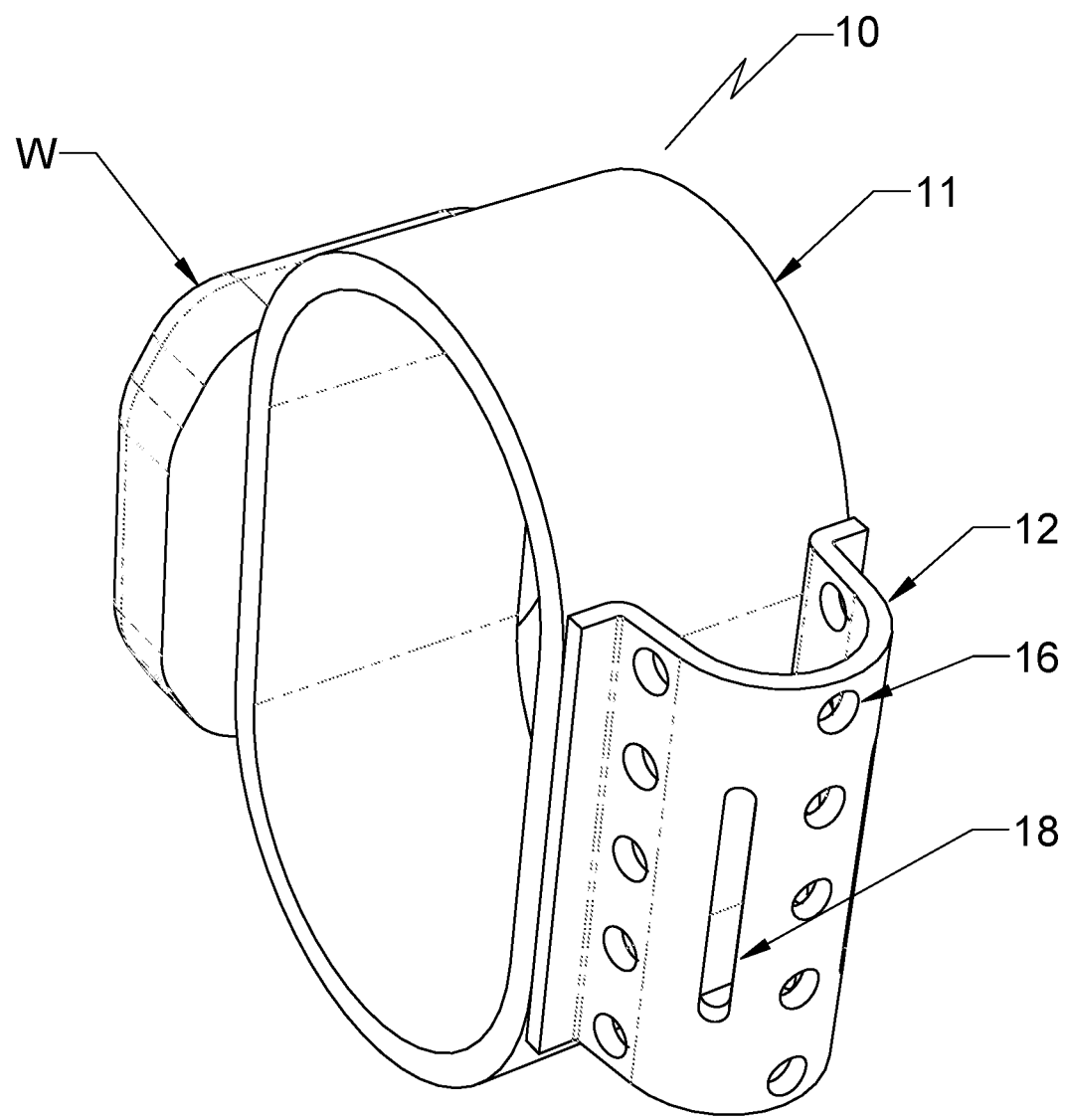
FIG. 4 is a view of the wristband illustrated in FIG. 1 with a close-up view of the sleeve for receiving an ammonium capsule and an assembly to crush the capsule.

As best viewed in FIG. 4, device 10 further comprises a sleeve 12 that is permanently attached. Sleeve 12 is designed to slidably receive an ammonia capsule AC and a cradle 14 for crushing the capsule. Sleeve 12 is generally of a half tubular shape and having a plurality of vent holes 16 for the ammonia vapor to vent. Sleeve 12 further includes a pair of slits 18. Sleeve 12 is made of an elastic material so that ammonia capsule AC and cradle 14 can be snugly fit between the sleeve and wristband 11.

Figure 2:
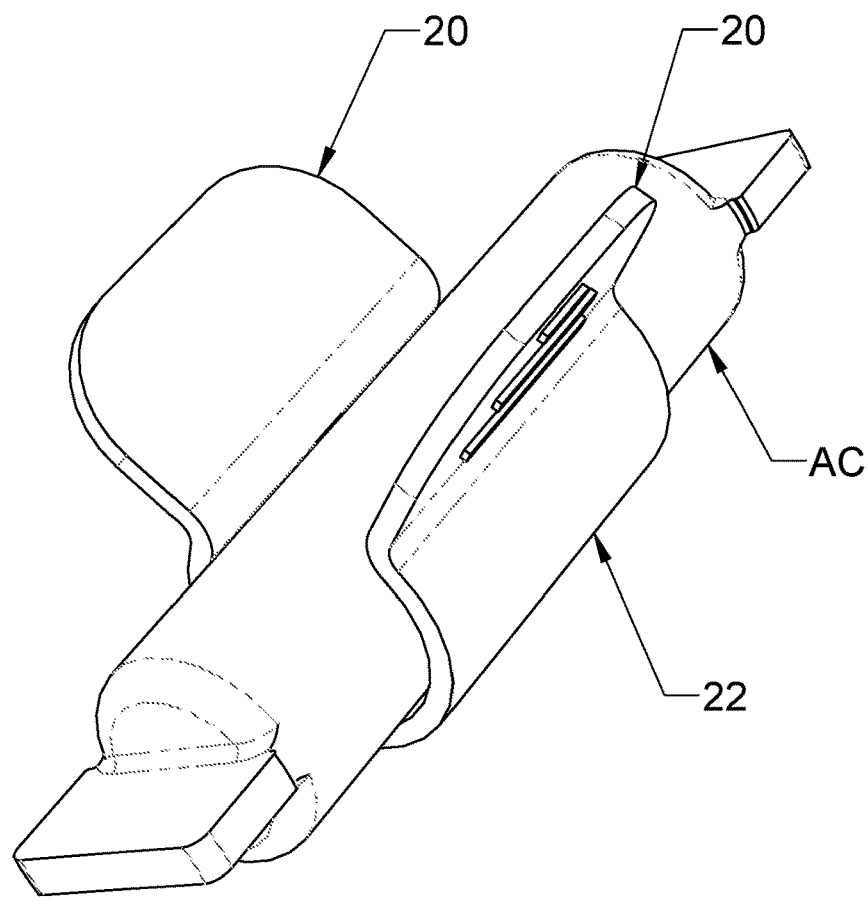
FIG. 2 is a perspective view of the assembly for crushing an ammonium vapor capsule.
Figure 3:
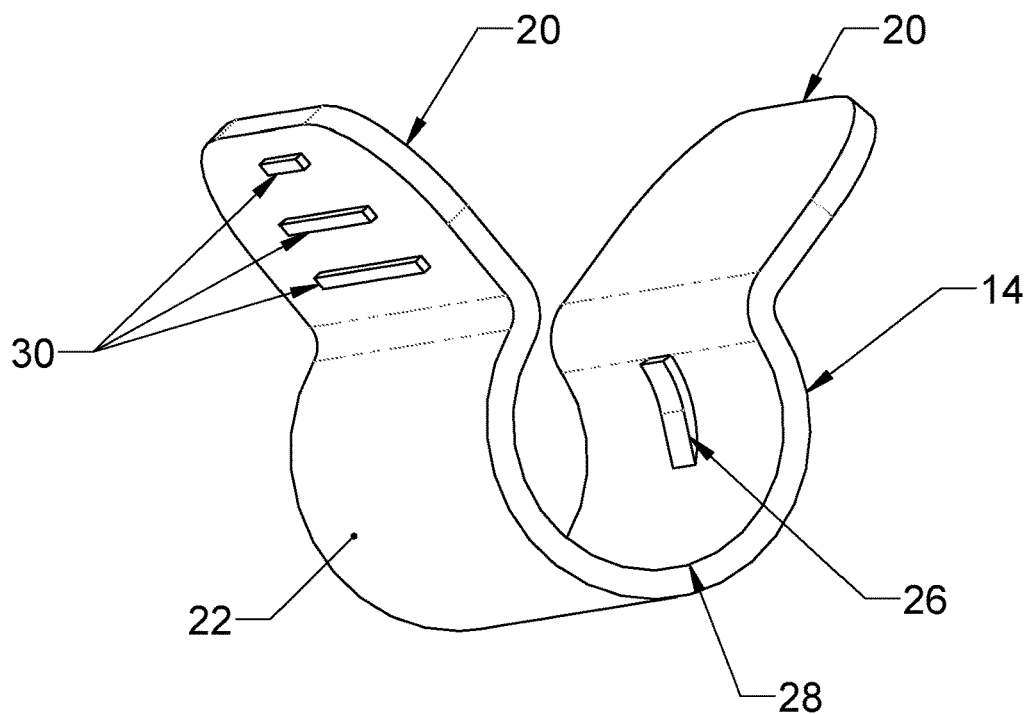
FIG. 3 is an alternative view of the assembly for crushing an ammonium vapor capsule.

FIG. 3 illustrates cradle 14 having a pair of flared ends 20 and a curved center portion 22. At least one projection 26 is present extending inward from the inner surface 28 of center portion 22. Friction ribs 30 are present on each wing for the wearer to easily grip each wing 20 with thumb and index finger. Cradle 14 is appropriately sized for an ammonia capsule AC to be positioned within as illustrated in FIG. 2. Projection 26 is present for fracturing ammonia capsule AC as will be described below.

Ammonium capsule AC is placed within cradle 14 as shown in FIG. 2. Next, sleeve 12 is stretched so that winged ends 20 are fitted through a respective slit 18 so that the relationship of the ammonium capsule AC to wristband 10 is as is shown in FIG. 1.

When a wearer senses a precipitous blood pressure drop, the wearer will place the index finger and thumb of the opposite hand upon respective flared ends 20 and in contact with friction ribs 30. Once in this position, the wearer pinches flared ends 20 toward one another with sufficient force to cause projection 26 to fracture capsule AC and release the ammonium vapor within the capsule.

The invention claimed is:

1. A device for releasing ammonium inhalant from a capsule comprising:
   a wristband;
   a sleeve formed of an elastic material, wherein opposite ends of the sleeve are attached to the wristband and wherein said sleeve further comprises two slits spaced apart from one another and, a plurality of vent holes to release the ammonium inhalant;
   a cradle comprising:
   a curved center portion having an inner surface including at least one capsule fracturing projection extending inward from the inner surface, the curved center portion sized to transversely receive the capsule containing the ammonium inhalant;
   flared ends extending from opposite ends of the curved center portion; and,
   wherein the curved center portion is positioned within said sleeve, and wherein each flared end extends through a respective slit of the sleeve.

2. A device for releasing ammonium inhalant from a capsule comprising:
   a wristband;
   a sleeve having opposite ends attached to the wristband and wherein said sleeve further comprises two slits spaced apart from one another and, a plurality of vent holes;
   a cradle comprising:
   a curved center portion having an inner surface including at least one capsule fracturing projection extending inward from the inner surface, the curved center portion sized to transversely receive the capsule containing the ammonium inhalant;
   flared ends extending from opposite ends of the curved center portion; and,
   wherein the curved center portion is positioned between the wristband and sleeve, and wherein each flared end extends through a respective slit of the sleeve coupling the cradle to the sleeve while the capsule remains in the transverse position in the cradle.

* * * * *